United States Patent
Hansen et al.

(10) Patent No.: US 9,655,690 B2
(45) Date of Patent: May 23, 2017

(54) PEDODONTIC/VETERINARY DENTAL CROWN SYSTEM

(71) Applicants: John P. Hansen, Loomis, CA (US); Jeffrey P. Fisher, Auburn, CA (US)

(72) Inventors: John P. Hansen, Loomis, CA (US); Jeffrey P. Fisher, Auburn, CA (US)

(73) Assignee: EZ PEDO, INC., Loomis, CA (US)

( * ) Notice: Subject to any disclaimer, the term of this patent is extended or adjusted under 35 U.S.C. 154(b) by 49 days.

(21) Appl. No.: 14/878,945

(22) Filed: Oct. 8, 2015

(65) Prior Publication Data

US 2016/0022378 A1 Jan. 28, 2016

Related U.S. Application Data (63) Continuation of application No. 13/568,195, filed on Aug. 7, 2012, now abandoned, which is a continuation-in-part of application No. 12/506,193, filed on Jul. 20, 2009, which is a continuation-in-part of application No. 12/228,783, filed on Aug. 14, 2008, now abandoned.

(60) Provisional application No. 60/964,912, filed on Aug. 15, 2007.

(51) Int. Cl.
*A61C 5/00* (2006.01)
*A61C 13/107* (2006.01)
*A61C 13/083* (2006.01)
*A61D 5/00* (2006.01)
*A61C 5/08* (2006.01)

(52) U.S. Cl.
CPC ............ *A61C 5/08* (2013.01); *A61C 13/0001* (2013.01); *A61C 13/083* (2013.01); *A61D 5/00* (2013.01)

(58) Field of Classification Search
CPC ..... A61C 5/08; A61C 13/0001; A61C 13/083; A61D 5/00
See application file for complete search history.

(56) References Cited

U.S. PATENT DOCUMENTS

| | | | | |
|---|---|---|---|---|
| 4,678,435 A | * | 7/1987 | Long | A61C 5/10 433/218 |
| 5,487,663 A | * | 1/1996 | Wilson | A61O 5/08 433/218 |
| 6,713,421 B1 | * | 3/2004 | Hauptmann | C04B 35/486 433/202.1 |
| 2002/0090592 A1 | * | 7/2002 | Riley | A61C 13/0001 433/173 |
| 2002/0150864 A1 | * | 10/2002 | Zilberman | A61O 5/08 433/218 |
| 2002/0168614 A1 | * | 11/2002 | Riley | A61C 13/0835 433/218 |

(Continued)

*Primary Examiner* — Cris L Rodriguez
*Assistant Examiner* — Hao D Mai
(74) *Attorney, Agent, or Firm* — Heisler & Associates (57) ABSTRACT

A dental crown consisting essentially of stabilized zirconia. The dental crown is particularly suited for pedodontic and veterinary applications and most preferably for pedodontic applications. The zirconia crown may be formed by one of several manufacturing processes. The formed crown exterior can be polished and fine polished and can be covered, preferably only partially, with a porcelain glaze to produce an aesthetic outer surface mimicking a natural tooth. Also disclosed is a method for providing and placing a dental crown upon a natural tooth.

20 Claims, 6 Drawing Sheets

(56) References Cited

U.S. PATENT DOCUMENTS

| | | | |
|---|---|---|---|
| 2003/0039943 A1* | 2/2003 | Worthington | A61C 5/08 433/218 |
| 2003/0194681 A1* | 10/2003 | Stoller | A61O 5/08 433/222.1 |
| 2004/0142305 A1* | 7/2004 | Harlan | A61C 13/0003 433/218 |
| 2006/0099552 A1* | 5/2006 | van der Zel | A61C 5/10 433/223 |
| 2006/0154211 A1* | 7/2006 | Bybee | A61C 5/08 433/218 |
| 2007/0196792 A1* | 8/2007 | Johnson | A61O 5/08 433/218 |
| 2008/0050700 A1* | 2/2008 | Weber | A61C 13/0004 433/202.1 |
| 2009/0004630 A1* | 1/2009 | van der Zel | A61O 5/10 433/223 |
| 2009/0286205 A1* | 11/2009 | Johnson | A61C 5/08 433/222.1 |
| 2010/0003641 A1* | 1/2010 | Hansen | A61C 13/083 433/218 |
| 2010/0028835 A1* | 2/2010 | Hansen | A61O 5/08 433/218 |
| 2010/0151423 A1* | 6/2010 | Ranck | A61C 13/0001 433/193 |
| 2010/0203480 A1* | 8/2010 | Schweitzer | A61C 13/0001 433/223 |
| 2010/0297587 A1* | 11/2010 | Zilberman | A61O 5/08 433/223 |
| 2012/0219930 A1* | 8/2012 | Heinz | A61C 3/02 433/215 |
| 2013/0130203 A1* | 5/2013 | Velamakanni | A61O 5/08 433/222.1 |
| 2013/0137064 A1* | 5/2013 | Velamakanni | A61O 5/10 433/222.1 |
| 2013/0137065 A1* | 5/2013 | Velamakanni | A61O 5/08 433/222.1 |
| 2013/0171589 A1* | 7/2013 | Velamakanni | A61O 5/08 433/222.1 |
| 2015/0245886 A1* | 9/2015 | Hegland | A61O 5/10 433/29 |
| 2015/0265380 A1* | 9/2015 | Sager | A61C 13/0004 433/169 |
| 2016/0135923 A1* | 5/2016 | Ahn | A61O 5/08 433/223 |
| 2016/0317395 A1* | 11/2016 | Velamakanni | A61K 6/0002 |

* cited by examiner

PEDODONTIC/VETERINARY DENTAL CROWN SYSTEM

CROSS-REFERENCE TO RELATED APPLICATIONS

This application is a continuation of U.S. patent application Ser. No. 13/568,195 filed on Aug. 7, 2012, which is a continuation-in-part of application Ser. No. 12/506,193 filed on Jul. 20, 2009, which is a continuation-in-part of application Ser. No. 12/228,783 filed on Aug. 14, 2008, which claims benefit under Title 35, United States Code §119(e) of U.S. Provisional Application No. 60/964,912 filed on Aug. 15, 2007.

FIELD OF THE INVENTION

The present invention relates to a novel and useful prefabricated crown for pedodontic and veterinary applications.

BACKGROUND OF THE INVENTION

At present, crowns used to repair adult human teeth are custom fabricated according to a mold of a tooth being repaired which is provided by the dental practitioner. The crowns may be formed of stainless steel or other metal clad with porcelain or a ceramic such as zirconia clad with porcelain. Using the mold as a guide, computer software, through a CAD/CAM technology, directs a milling machine to mill a coping or framework of the crown out of the chosen material, such as metal or ceramic, which is eventually clad with porcelain. Although satisfactory in result, the patient receiving such a crown must make multiple visits to the dental office to achieve this result and the process is time-consuming and expensive. The foregoing procedure is particularly difficult when the tooth being replaced is a child's (baby) tooth which will eventually be lost and replaced by permanent teeth through the natural maturing process. Veterinary crowns are also produced in the same manner and can be just as difficult to produce.

Given the difficulties of dealing with a child in a dentist's chair, dentists have developed prefabricated crowns that do not require molds and multiple visits to the dentist. The use of prefabricated, stainless steel crowns for restoring badly broken-down children's teeth is now the standard of care in pediatric dentistry. Recently, the American Academy of Pediatric Dentists has encouraged crown restorations due to the poor outcomes resulting from the use of fillings in certain high-risk groups, especially children with the inability to cooperate in the dental chair, thereby necessitating the use of general anesthesia for their dental treatment. Prefabricated crowns are a very efficient and reliable restoration resource and are the restoration of choice in teeth with moderate to severe dental decay.

Stainless steel prefabricated crowns are the most versatile and widely used crowns in pediatric dentistry. However, due to their unaesthetic appearance, many dentists are turning to other manufacturers of preformed pediatric crowns for a more aesthetic option for their patients. In the late 1980's, the idea of creating a stainless steel crown and covering the visible surface with a tooth-colored composite material veneer started to gain favor. Cheng Crowns (1987), Kinder Krowns (1989), and NuSmile Crowns (1991) are some of the most notable manufacturers to gain significant market share with this revolutionary new crown for pediatric dentistry. Although these new crowns were much more aesthetic than the all-stainless-steel crowns, they came with some significant drawbacks.

The main benefit of the pre-veneered crowns was their more aesthetic appearance compared to their stainless steel predecessors. This new product, however, required a new method for preparing the tooth and seating the crowns. Because the plastic material was bonded to the metal substructure, it was recommended that these restorations have a passive fit to the tooth, minimizing the potential to crack the facing. Crimping or altering the metal substructure, which dentists were accustomed to doing before seating a crown, is not recommended in order to avoid weakening the bond between metal and facing. However, due to the increased strength of modern cements, this passive fit method has become accepted and works quite well with most luting agents used on the market today.

However, because of the interface between the metal and the plastic facing, there is also a tendency for the facing material to crack or chip off the metal substructure. The fragile nature of this interface is a major negative. Dentists often crack a facing when seating the crown or are required to re-treat a returning patient because of an unsightly failed restoration caused by the failure of this weakened interface.

Since the plastic facing must be applied to the front of the tooth over the metal substructure, the facing has a very bulky and bulbous appearance. This is particularly noticeable when the need arises to crown only one anterior tooth. It is very hard to match the contour of the patient's natural teeth when using these bulky crowns, necessitating a significant reduction of the tooth structure in order to ensure a proper fit which can lead to unnecessary involvement of the pulp chamber and the need to perform a pulpotomy on the tooth.

Figure 11:
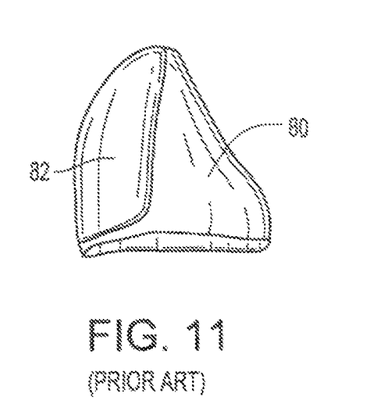
FIG. 11 is a perspective view of a prior crown made of stainless steel with a polymeric coating.

FIG. 11 shows a perspective view of one such bulky crown comprising a stainless steel base 80 and polymeric coating 82.

Matching tooth color is another big challenge when using current aesthetic pediatric crowns. The nature of the plastic overlaying the metal substructure gives them their nickname of "Chiclets." This is a word that is used frequently by both dental professionals and parents when describing the appearance of the current crowns available on the market.

In the course of sizing the crowns on the teeth to ensure proper fit, it is often necessary to sterilize and restock the unused crowns. The use of heat sterilizing techniques weakens the facing and the overall integrity of the crown. Therefore, it is necessary to use a 24-hour cold sterilizing technique on these crowns because of their plastic facing/metal interface. However, the use of the cold sterilizing technique tends to alter the shade of the facing from its original color. Due to this fact, many offices must maintain a separate storage container for crowns that have been sterilized. As the sterilized crowns will often not match those that have never been tried in the mouth, dental offices must stock a larger inventory of crowns which is a major unnecessary disadvantage for the dentist.

Even with all the potential negatives to these aesthetic crowns, until now they have been the best alternatives for dentists and parents who want a more natural smile for their children.

Various ceramics have been used in dentistry. Alumina, for example, has been used for implant abutments and crown and bridge frameworks and copings. Alumina has more translucency and better matches the translucency of natural teeth, but it lacks in strength and is more prone to failure.

Zirconia formulations have been used in adult dentistry for several years as a replacement for metal for the manufacturing of crown coping or frameworks. The copings are typically layered with porcelain to build up the entire structure of the tooth restoration and to develop the aesthetic surface characteristics. Zirconia has also been used for implant abutments and as endosseous implant cylinders. Zirconia is white in color, and extremely strong. Zirconia has been replacing alumina as the framework material of choice due to its strength. The downside of zirconia is that it is very bright white and by itself, does not match the human dentition well.

Dental crowns and impression systems of various sorts have been proposed in the past. For example, U.S. Pat. No. 6,769,913 describes a device for taking dental impressions. The device includes impression cap having an injection port configured to receive material in an inner cavity.

U.S. Pat. No. 4,492,579 shows a dental crown substrate formed of a noble-based metal formed over a thin metal foil substrate. A veneering material such as porcelain is then coated over the substrate.

U.S. Pat. Nos. 4,992,049, 5,314,335, and 5,538,429 teach dental crowns utilizing a base of metallic mesh or stranded material covered by a veneer of porcelain.

U.S. Pat. Nos. 3,058,216, 3,375,582, 4,392,829, 4,846, 718, 5,624,261, 6,106,295 and 7,008,229 describe dental crowns utilizing metal or plastic as a coping which is veneered by porcelain or plastic material.

U.S. Pat. No. 6,663,390 illustrates a ceramic prosthesis in which a metallic core is provided for attachment to an implant in the patient's mouth. A ceramic crown of porcelain zirconia, or polymeric material then covers the extending metallic core.

U.S. Pat. No. 1,609,549 shows a telescopic tooth crown in which the interior of the crown includes a number of indents to aid in the adhesion of the inner and outer shells of the crown.

U.S. Pat. No. 4,766,704 discloses machining a crown from a ceramic blank.

United States Published Patent Application No. US2006/0154211 describes a pediatric crown which may be prefabricated in various sizes and shapes for primary dentition. Porcelain has been employed as a outer crown material due to aesthetic appeal.

U.S. Pat. No. 6,638,069 shows a shaping cap using a matrix material including fillers such as zirconia mixed with silica and titanium dioxide.

U.S. Pat. No. 5,775,913 shows an acrylic material filled with quartz or silicon dioxide, called Artglass.

U.S. Pat. No. 6,592,373 shows a crown formed form an injection molded acetal homopolymer.

U.S. Pat. No. 6,974,323 describes a micromechanically acting retention pattern formed by a laser in a zirconia composition implant abutment and dental restoration.

WO 2007/046693 describes a method for increasing the bond strength of stabilized zirconia to another substance.

The disclosures of each of the above references are incorporated by reference herein.

A pre-fabricated strong crown for pedodontic and veterinary applications and process for making the same would be a notable advance in the dental field.

SUMMARY OF THE INVENTION

In accordance with the present invention, a novel and useful crown for pedodontic and veterinary applications is herein provided, most preferably for pedodontic applications.

The present invention provides a dental crown composed of substantially pure zirconia ($ZrO_2$) to create a strong crown. The zirconia is stabilized with stabilizers including, but not limited to, magnesium oxide (MgO), calcium oxide (CaO), yttrium oxide ($Y_2O_3$), cerium oxide ($CeO_2$), aluminum oxide ($Al_2O_3$), scandium oxide ($Sc_2O_3$), ytterbium oxide ($Yb_2O_3$) and hafnium oxide ($HfO_2$). Preferably, the zirconia crown is formed by designing in CAD (Computer Aided Design) followed by milling of sintered stabilized zirconia. Other methods of manufacturing the zirconia crown include electrophoretic deposition, ceramic injection molding or slip casting.

Various sizes of pedodontic and veterinary crowns may be pre-fabricated for children and animals.

In addition, the interior surface of the crown preferably includes at least one retention feature which assists in a lasting bond of the crown to the stub of the natural tooth.

Zirconia possesses a fairly, although not perfect, natural white color. The zirconia crown prepared as described above may be further amplified aesthetically to closely match dental teeth by creating a pearlescent outer surface. Such a result is achieved by pre-polishing the external surface of the cast zirconia crown with a diamond impregnated silicon wheel. A final polish is then accomplished by a brush wheel with the application of a diamond paste prior to placement in a patient. In addition, color modifiers may be added to the zirconia before sintering to modify the color of the zirconium.

Further, for better tooth appearance, the zirconia crown may be partially coated on the front portion of the crown with a porcelain glazing material. The glazing material presents a more natural tooth appearance. It may be desirable to color the glazing material for an even more natural tooth appearance.

After the crown has been created, crowns of various sizes may be placed in a kit for use by the dental practitioner. In this regard, the practitioner follows standard preparation guidelines for primary dentition for placement of a pre-fabricated crown. Thus, a pedodontic crown may be installed or placed on a natural tooth in a single visit simply by preparing the tooth stub, and selecting a proper size of a pre-fabricated zirconia crown by its mesiodistal width. The selected crown is then evaluated for fit and possible tissue impingement. A passive fit is preferred where the selected crown may fit loosely on the tooth stub which may not touch the selected crown. Although uncommon to do, any extension of gingival margin is then trimmed where necessary with a fine diamond at relatively slow speed and with copious water spray. The crown is then filled with glass ionomer or self curing composite resin cement which will fill the large gap between the selected crown and the tooth stub. The crown is then seated in the mouth completely. It should be noted that the at least one retention feature in the zirconia crown greatly aids in the fixing of the same to the stub of the natural tooth. Following such seating, the orientation of the crown is checked. The emplaced crown is as hereinabove described mimics a natural tooth in appearance.

While the present invention is directed to pedodontic and veterinary crowns, and most preferably pedodontic crowns where the present invention offers the greatest advantages, the teachings of the present invention may have applicability to adult crowns. The present crowns may also be used for adults but in this case, the crowns may have a tight fit where the crown fits snugly on the adult tooth stub. There may be a small cement gap that is filled with cement.

It should be realized that a new and useful dental crown system has been hereinabove described.

OBJECTS OF THE INVENTION

Accordingly, a primary object of the present invention is to provide a pedodontic and veterinary crown which is simple to use and easy to manufacture.

Another object of the present invention is to provide a pedodontic and veterinary crown in which the crown is essentially formed of stabilized zirconia.

Another object of the present invention is to provide a pedantic and veterinary crown that is only partially glazed to mimic the natural tooth appearance of a patient.

Another object of the present invention is to provide a pedodontic and veterinary crown in which a zirconia crown is employed that possesses great strength and durability.

Yet another object of the present invention is to provide a zirconia dental crown which is suitable for use with front and rear natural teeth.

Another object of the present invention is to provide a dental crown composed solely of stabilized zirconia whose outer surface has been altered to closely resemble the appearance of a natural tooth.

A further objective of the present invention is to provide a pedodontic and veterinary dental crown which overcomes the problems of durability, non-uniformity, and the like of prior pedodontic dental crowns.

Other further objects of the present invention will become apparent from a careful reading of the included drawing figures, the claims and detailed description of the invention.

BRIEF DESCRIPTION OF THE DRAWINGS

FIG. 8A is a side view of a dental crown according to the present invention while

DESCRIPTION OF THE PREFERRED EMBODIMENT

Various aspects of the present invention will evolve from the following detailed description of the preferred embodiments thereof which should be referenced to the prior described drawings.

The present invention is directed to pedodontic and veterinary crowns and to a method of providing pedodontic and veterinary crowns for a natural tooth. Pedodontic and veterinary crowns shall be collectively referred to hereafter in the following description as just crowns.

While the discussion that follows may apply to both pedodontic and veterinary crowns, it should be understood that the present invention is most preferably applicable to pedodontic crowns for restoring baby teeth in patients that are approximately 2 to 10 years old. Baby teeth are temporary teeth which the pedodontic patient eventually loses and are replaced with permanent teeth.

The ideal crown should have the following characteristics:

It would be strong and durable;

It would be made of one material to eliminate the problems associated with the fracturing of the aesthetic facing;

It would be thin, like a stainless steel crown, to insure the best emergence profile and overall natural appearance of the tooth. This thinness would also facilitate more conservative preparation of the stump tooth, and therefore reducing chances for nerve damage and increasing retention of the restoration;

It would meet aesthetic scrutiny by having a natural color and surface shine that would mimic adjacent natural teeth;

These crowns would be able to be sterilized with the auto clave for fast turnaround time without the fear of color alteration or compromise of structural integrity;

The method for use would be the same as that used for crowns currently on the market, avoiding the need for dramatic changes in clinical technique; and The ideal crown would be available in a variety of sizes and at a cost that was competitive in today's market.

The crowns according to the present invention meet the above characteristics.

Figure 1:
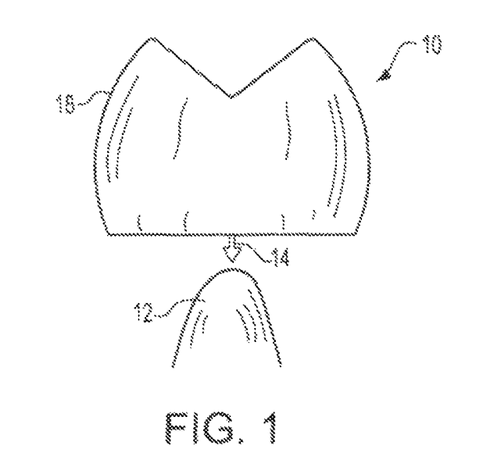
FIG. 1 is a side elevational view of the dental crown of the present invention with a directional arrow indicating its installment on a tooth stub.
Figure 2:
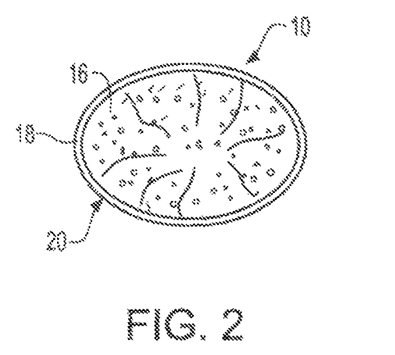
FIG. 2 is a top plan view of the dental crown of the present invention.

Referring to the Figures in more detail, and particularly referring to FIGS. 1 and 2, the invention as a whole is shown in the drawings by reference character 10. The crown 10 is intended to fit over the stub 12 of a natural tooth and is placed in that position according to directional arrow 14. Dental crown 10 includes an inner surface 16, of FIG. 2, and an outer surface 18. Crown 10 is a monolithic structure essentially composed of stabilized zirconia which has been treated to closely follow the color and appearance of a natural tooth. By monolithic, it is meant that crown 10 is only composed of the stabilized zirconia composition and there are no exterior veneer layers of porcelain or plastic. As the crown 10 is sized to fit directly on the patient's tooth stub, there are no exterior veneer layers or interior layers of any type (other than cement) or interior appliances such as a coping or implant abutment. Further, the crown 10 is formed to be in a net shape for placement on a tooth stub without modification of the dimensions of the crowns 10, although, while uncommon, it may be necessary to adjust the gingival margin of the crown 10. When the crown 10 is placed on the patient's natural tooth using a passive fit (i.e., a very loose fit) for a pedodontic crown, the patient only sees the surface of the stabilized zirconia crown as layering of a plastic or porcelain veneer as shown in the prior art (FIG. 11) does not occur with the present invention. The passive fit should be distinguished from a tight fit when a dental crown may be placed on an appliance such as an implant abutment which requires a very tight and intimate fit between the implant abutment and the dental crown. In this latter case, the dental crown and implant abutment are made as a matched set with an intimate and tight fit and a small, uniform cement gap.

The stabilized zirconia may consist of 85 to 99.9 weight percent of zirconia and 0.1 to 15 weight percent of stabilizer which may include, but not be limited to, magnesium oxide (MgO), calcium oxide (CaO), yttrium oxide ($Y_2O_3$), cerium oxide ($CeO_2$), aluminum oxide ($Al_2O_3$), scandium oxide ($Sc_2O_3$), ytterbium oxide ($Yb_2O_3$) and hafnium oxide ($HfO_2$). The presence of the stabilizer is believed to increase the strength of pure zirconia by presenting formation of a monoclinic crystal structure. Included within the foregoing 0.1 to 15 weight percent may be small elements of other compounds such as iron oxide (Fe2O3) or titanium oxide (TiO2) for coloration purposes.

Inner surface 16, takes the form of a hollowed out area which is intended to fit the stub 12 of the natural tooth. In addition, the interior surface 16 of crown 10 includes at least one retention feature which assists in holding the crown 10 to the tooth 12. Such a retention feature is important for the following reason. Once sintered, zirconia has a smooth surface finish. This smooth surface finish is satisfactory for the outer aspect of the restoration which will be polished, however, the inside of the restoration is better if it is not smooth.

Metal and ceramic restorations are typically microblasted with abrasive particles and air, and ceramic restorations are then additionally hydrofluoric acid etched to further roughen the internal aspect. Roughening the surface allows better mechanical retention of the cement layer. However, sintered zirconia, unlike traditional dental ceramics and porcelains, is too hard to be air abraded and does not etch with hydrofluoric acid. Furthermore, if the zirconia is drilled on by the dentist to add grooves, the heat generated can weaken and fracture the zirconia molecular structure. All manufacturers of zirconia restorations do not recommend drilling on the zirconia for that reason, unless it can be put back into the sintering furnace to heal any fractures. This is impossible in a clinical situation since sintering takes many hours and requires a special furnace of over 1000 degrees centigrade.

Figure 6:
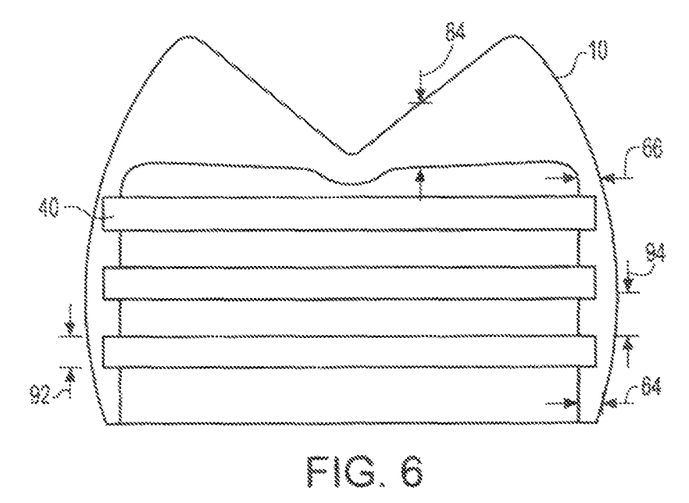
FIGS. 6 and 7 are sectional views of another embodiment of the dental crown showing retention features.
Figure 7:
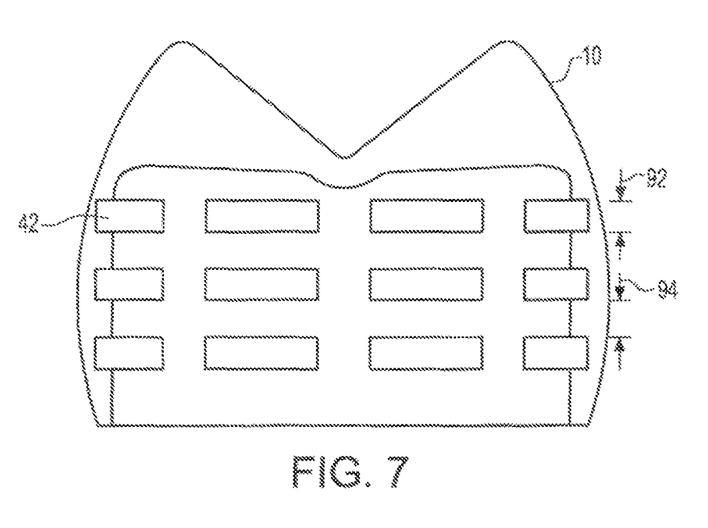

The present inventors have proposed a preferred novel step over milling process which creates macroscopic apertures on the inside of the restoration to aid in retention by locking in the cement layer. The step over milling process can create spirals, grooves, random cuts, indentations or other designs to help improve retention of the cement layer to the restoration. Shown in FIG. 6 is a cross section of a crown in which grooves 40 are cut into the interior surface 16 while FIG. 7 is a cross section of a crown in which ledges or short segments 42 are cut into the interior surface 16. The grooves 40 and short segments 42 should have a width 92 of about 0.05-0.7 mm and a depth of about 0.05-0.4 mm. In addition, the groves 40 and short segments 42 should be spaced apart 94 from each other by about 0.05-0.7 mm. Alternative retention features may include a plurality of holes or pits 20 in the interior surface 16 of the crown 10 which create interstices to accept cementitious material when the crown 10 is eventually placed over tooth stub 12 and allowed to set. Such retention features help to retain the crown 10 on the tooth 12.

Figure 8A:
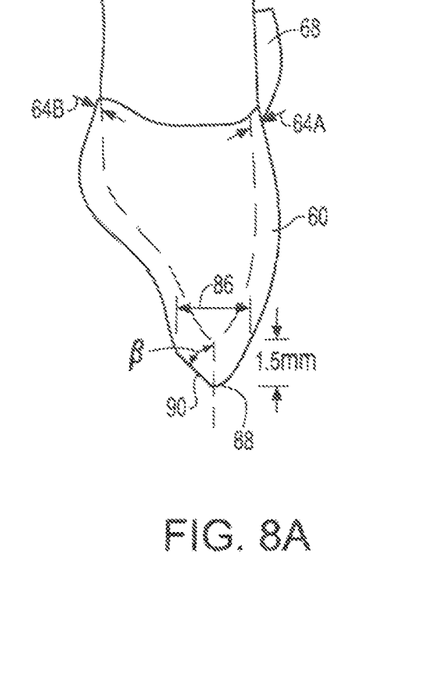
Figure 8B:
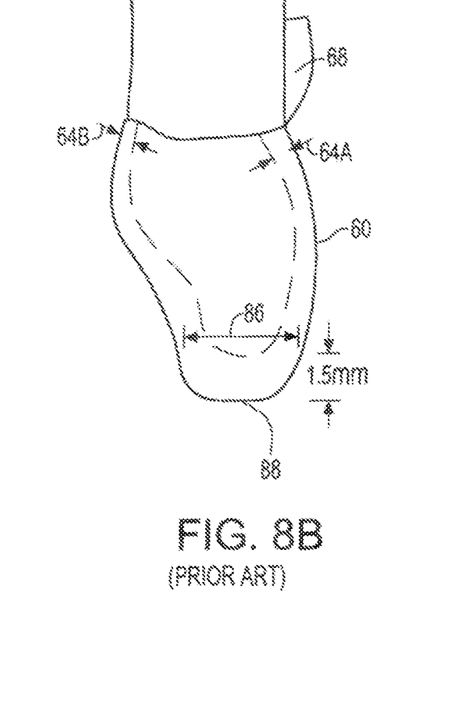
FIG. 8B is a side view of a dental crown according to the prior art.

Since the crowns according to the present invention are not made by a layering process wherein plastic or porcelain veneer is layered over a metal crown, the crowns according to the present invention can be kept thin at the incisal edge. Referring to FIGS. 8A and 8B, a conventional crown is on the right (FIG. 8B) and the inventive crown is on the left (FIG. 8A). It can be seen that the incisal edge 88 which is determined by measuring the last 1.5 mm of the biting edge buccolingually (lip side to tongue side of the tooth) across the crown as indicated by 86 is about 2.5-3.5 mm for the prior art crown and is about 0.4-2.0 mm for the crown of the present invention. This indicates that the prior art crown has a more rounded and undefined incisal edge 88 which reduces the cutting efficiency of the tooth. Also important to note is that the crowns of the present invention have a bevel 90 on the lingual side of the tooth which give the crowns of the present invention more of a cutting edge like a natural tooth. The angle β of the bevel should be about 28 to 70 degrees measured from the vertical as shown in FIG. 8A.

Figure 12:
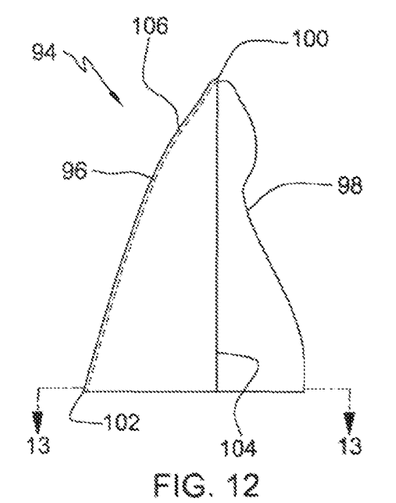
FIG. 12 is a side view of a dental crown for an anterior tooth according to the present invention.

In an exemplary embodiment, the dental crowns may have an aesthetic glaze that covers only part of the dental crowns. Referring now to FIG. 12, there is shown a first dental crown 94 for an anterior tooth that has a front surface 96 (buccal surface) that faces outwardly to the front of the patient's mouth and a rear surface 98 (lingual surface) that faces toward the patient's tongue. The front surface 96 may contain a glaze 106 that extends from the biting surface 100 to the margin 102 and wraps about half-way around the crown 94 stopping at 104.

Figure 13:
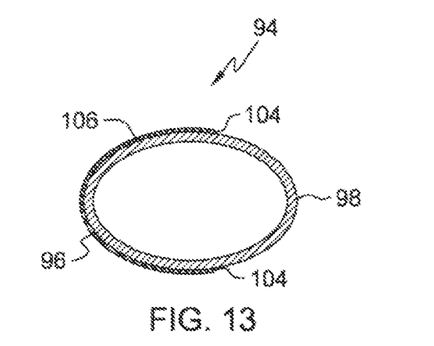
FIG. 13 is a cross-sectional view of the dental crown in FIG. 12 in the direction of arrows 13-13.

A cross section of dental crown 94 in the direction of arrows 13-13 is shown in FIG. 13. The glaze 106 wraps approximately half-way around the circumference, stopping at 104. Glazing the rear surface 98 is undesirable as it can cause abrasion of the opposing anterior tooth.

The dental crown 94 may be polished to have a pearlescent polished surface except where the glaze 106 is present. That is, the pearlescent polished surface may be the rear surface 98 (extending around and stopping at 104) while the glaze 106 will be on the front surface 96. The glaze 106 presents a surface appearance that greatly mimics the natural tooth appearance of a patient. Since it is the front surface 96—that is, the glaze surface —that the patient and others may see while looking at the patient, the appearance of the dental crown 94 with the glaze 106 presents a more natural, pleasing appearance to the patient and others.

Figure 14:
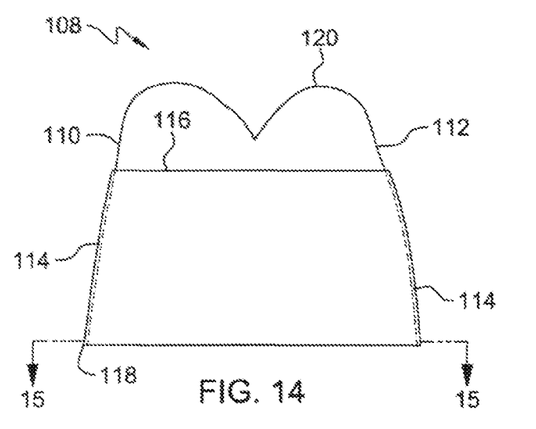
FIG. 14 is a side view of a dental crown for a posterior tooth according to the present invention.

Referring now to FIG. 14, there is shown a second dental crown 108 for a posterior tooth that has a front (buccal) surface 110 and a rear (lingual) surface 112. The front surface 110 may contain a glaze 114 that extends from a line 116 just below the biting surface 120 to the margin 118 and wraps around the rear surface 112 of the crown 108. In an embodiment that is not as preferred, the glaze 114 may only wrap half-way around the dental crown. The glaze 114 preferably should not be on the biting surface 120 since it is abrasive and can cause unusual wear on the opposing posterior tooth.

Figure 15:
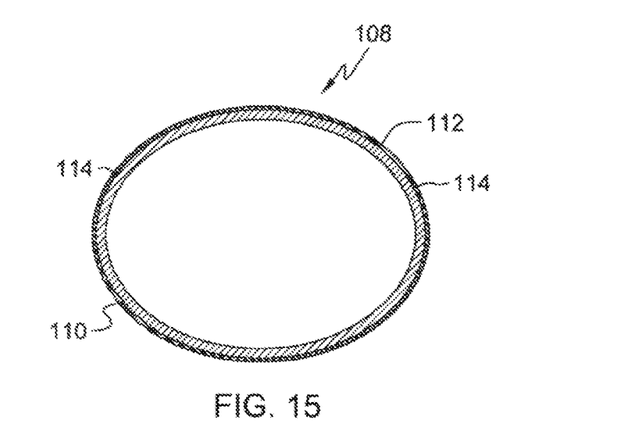
FIG. 15 is a cross-sectional view of the dental crown in FIG. 14 in the direction of arrows 15-15.

A cross section of dental crown 108 in the direction of arrows 15-15 is shown in FIG. 15. The glaze 114 wraps around the entire circumference of the dental crown 108.

Again, the dental crown 108 may be polished to have a pearlescent polished surface except where the glaze 114 is present. The pearlescent polished surface ay also include the biting surface 120.

The purpose of the glaze 106, 114 is for aesthetics only to present a more pleasing appearance for the patient.

In the prior art embodiments where there is a porcelain or plastic veneer over a ceramic or metal core, the veneer may have a thickness of around 0.5 to 1.5 millimeters and as explained previously, results in a restoration that is not aesthetically pleasing and may result in chipping or spalling of the porcelain or plastic veneer.

The glaze 106, 114 is much thinner, on the order of 0.005 to 0.1 millimeters. More preferably, the thickness range of the glaze 106, 114 should be at a minimum 0.02 millimeters to provide sufficient coverage and wear resistance and at a maximum 0.06 millimeters which should provide sufficient wear resistance and aesthetics without being too thick. With the glaze 106, 114 being so thin, the shape of the crowns 94, 108 are not affected by the glaze 106, 114. Also, the glaze 106, 114 will not chip or spall off the crowns 94, 108.

The dental porcelains that may be used for veneers or even for the entire crown are usually composed of kaolin clay (may also be in the form of kaolinite ($Al_2Si_2O_5(OH)_4$), a feldspar and some additional proprietary ingredients formulated by the suppliers of the dental porcelains. Feldspars are aluminosilicates, frequently alkali aluminosilicates, and may have the compositions $KAlSi_3O_8$, $NaAlSi_3O_8$ or $CaAl_2Si_2O_8$. These dental porcelains containing feldspar may also be called feldspathic porcelains. Porcelains other than feldspathic porcelains known to those skilled in the art may be used in the exemplary embodiments. In particular, dental porcelains other than feldspathic porcelains that bond to stabilized zirconia may be used in the exemplary embodiments although feldspathic porcelains right now are the preferred porcelains for use in the exemplary embodiments.

The glaze 106, 114 may be made by diluting a dental porcelain in water or organic solvent and then applying it as a very thin layer. Glazes may come premixed, in a paste or in powder form. If in powder form, the glaze powder and the solvent provided by the manufacturer may be mixed together until the desired consistency is obtained. The precise composition of the glaze may not be known as it is often a proprietary formulation by the glaze manufacturer.

It is preferred that feldspathic porcelains be used in the exemplary embodiments. Again, the glaze 106, 114 is several orders of magnitude thinner than a porcelain veneer and is not subject to the chipping and spalling problems of porcelain veneers.

The process for applying the glaze 106, 114 may be as follows. The dental crowns 94, 108 are microabraded using 50 micron alumina particles where the glaze is to be formed. The microabrasion roughens the surface of the stabilized zirconia crowns 94, 108. Microabrasion is preferred to allow the diluted porcelain solution to wet the surface of the zirconia. Without the microabrasion, the diluted porcelain solution may simply bead up on the surface of the stabilized zirconia. The diluted porcelain solution may then be applied, such as by painting with a fine brush, to the desired portion of the dental crowns 94, 108, preferably that portion that has been microabraded. In the case of the dental crown 94 for an anterior tooth, it may be applied only to the front 96 of the dental crown 94. In the case of the dental crown 108 for a posterior tooth, it may be applied only to a portion of the front 110 and rear 112 of the dental crown 108, preferably that portion that has been microabraded. Thereafter, the dental crowns 94, 108 may be fired at a temperature of about 850° C. for about 25 minutes to cause the diluted porcelain solution to form the glaze 106, 114.

The stabilized zirconia material of the dental crowns 94, 108 is chemically inert so that the glaze 106, 114 does not chemically bond with the stabilized zirconia. However, quite surprisingly and unexpectedly, the glaze 106, 114 forms a strong mechanical bond with the stabilized zirconia. While not wishing to be held to a particular theory, it is believed that the glaze 106, 114 shrinks during firing, mechanically locking the glaze 106, 114 onto the underlying stabilized zirconia of the dental crowns 94, 108.

Figure 9:
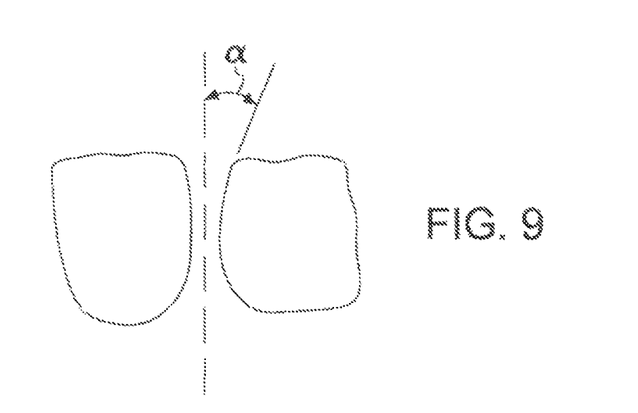
FIG. 9 is a frontal view of natural teeth demonstrating the interproximal line angle.

The crowns according to the present invention have been designed so that they have a normal emergence from the root structure. Referring to FIG. 9, the inventive crowns have an interproximal line angle, a, of 5 to 12 degrees to allow for a healthy interproximal papilla. The prior art crowns do not allow for such an angle, thereby causing problems for the patient later on.

The crowns according to the present invention have a facial profile similar to that of normal teeth. Referring back to FIG. 8, it can be seen that both teeth have a convex facial profile 60 but the inventive crown is much less convex and more in line with a normal curvature of a natural tooth.

The crowns according to the present invention use zirconia that has been specially formulated so that it is strong, aesthetic and, most importantly, thin. These properties enable the best of both worlds—room on the inside for passive fit, and contours on the outside of the crown that blend in with the natural tooth shape. Since the inventive crown is thinner than the current aesthetic crowns, the restoring dentist will not have to prepare the tooth as much, allowing for more retention and decreased chance of damage to the nerve. Referring back to FIG. 6, the approximate thickness of the crown axially as indicated 64 is about 0.1 to 0.4 mm while the approximate thickness of the crown from the axial-occlusal line angle to the occlusal surface as indicated at 66 is about 0.4 to 0.8 mm. These should be compared to the prior art aesthetic crown whose thickness of the crown axially on the buccal side is about 0.5-2.0 mm (64 in FIG. 6 for the inventive crown) and of the crown from the axial-occlusal line angle to the occlusal surface (66 in FIG. 6 for the inventive crown) on the buccal side is about 0.8-2.5 mm. The thick crown wall of the prior art aesthetic crown creates a dilemma for the dentist. The tooth has to be aggressively prepared so that the thick walled prefabricated pediatric crown will fit passively on the tooth stump. In the situation for baby teeth, the tooth is small already, and grinding them more to allow for the thickness of the crown increases the chance that the crown will fall off after it is cemented, or cause permanent damage to the nerve of the tooth.

The crowns according to the present invention have a thin margin, again indicated by 64 in FIG. 6, of about 0.1-0.4 mm around the circumference of the opening of the crown 10. Referring to FIG. 8A, the margin 64 is about 0.1-0.4 mm on both the buccal side 64A and the lingual side 64B. The advantage of a thin margin is that the margin can fit under the gum 68 as shown in FIG. 8. With the prior art crown, shown in the right half of FIG. 8, the margin may not fit under the gum 68, since the prior art crown has a margin thickness of about 0.5-1.5 mm on the buccal side 64A even though the margin 64B on the lingual side may be 0.2-0.4 mm, thereby causing the margin 64A to impinge on the gum tissue 68, potentially creating inflammation and swelling.

Referring back to FIG. 6, the crowns according to the present invention have a thickness of the occluasal surface 84 of about 0.5-0.9 mm while the prior art crowns have a thickness of the occlusal surface of about 0.8-2.5 mm.

Figure 10A:
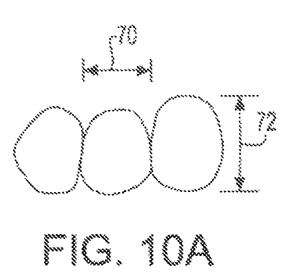
FIGS. 10A, 10B and 10C are plan views showing the crowding that can occur with tooth decay and resulting mesiodistal dimension decrease.
Figure 10B:
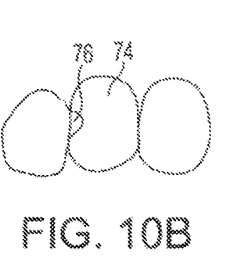
Figure 10C:
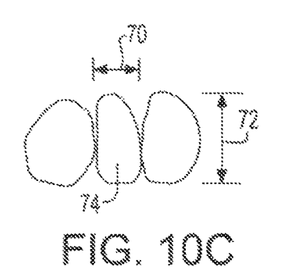

A further advantage of the present invention is that crowns can be prefabricated with a normal mesiodistal dimension as well as a reduced mesiodistal dimension as might be needed because of space loss due to decay. When teeth decay and loose tooth structure, the space that is created from the loss of tooth structure allows the adjacent teeth to drift and fill in the space. Referring to FIG. 10A, three normal child's teeth are shown. The mesiodistal dimension is indicated by 70 while the buccolingual dimension is indicated by 72. In FIG. 10B, the middle tooth 74 has some tooth decay 76. Over time, the adjacent teeth can crowd tooth 74 so that the mesiodistal dimension 70 could be reduced as shown in FIG. 10C while the buccolingual dimension stays the same. Current preformed pediatric crowns do not fit properly in this situation as they are too wide mesiodistally for the appropriate buccolingual dimension. The dentist has to squeeze the preformed crown mesiodistally to make it fit and it ends up bulging out buccolingually. The inventive crown is offered in alternative sizes wherein the standard size has been modified to be narrower mesiodistally while keeping the normal size buccolingually. This allows a better fit in space loss secondary to caries and tooth migration situations.

Figure 3:
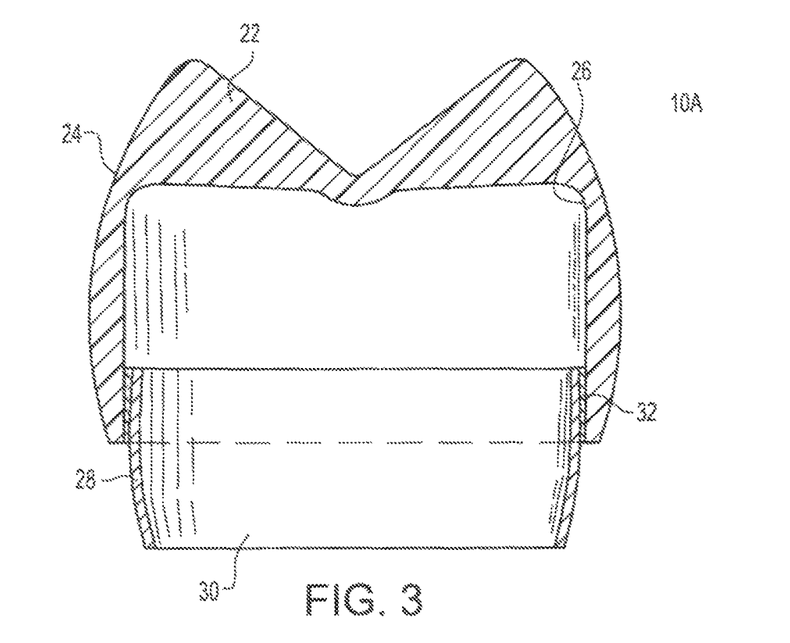
FIG. 3 is a sectional view of another embodiment of the dental crown of the present invention.

With respect to FIG. 3, another embodiment 10A of the present invention is depicted. 10A includes a crown 22 formed similarly to crown 10 of FIGS. 1 and 2, namely being composed substantially of pure zirconia. Crown 22 includes an outer surface 24 and an inner surface 26. In addition, embodiment 10A is formed with an inner band or sleeve 28 which is flexible. The edge portion 30 of sleeve 28 may be cut and/or crimped to fit cervical margins during preparation of the natural tooth. Sleeve 28 may be formed of any suitable material such as metal, plastic, and the like. For example, stainless steel may be employed in this regard. Sleeve 28 is bonded to inner surface 26 of crown 22 via an adhesive layer 32. Adhesive layer 32 may consist of Panavia F or other suitable bonding agents. Embodiment 10A of the present invention can be employed on the rear teeth of a patient, while the embodiment 10, depicted in FIGS. 1 and 2, can be used on the front or rear teeth of a patient.

Figure 4:
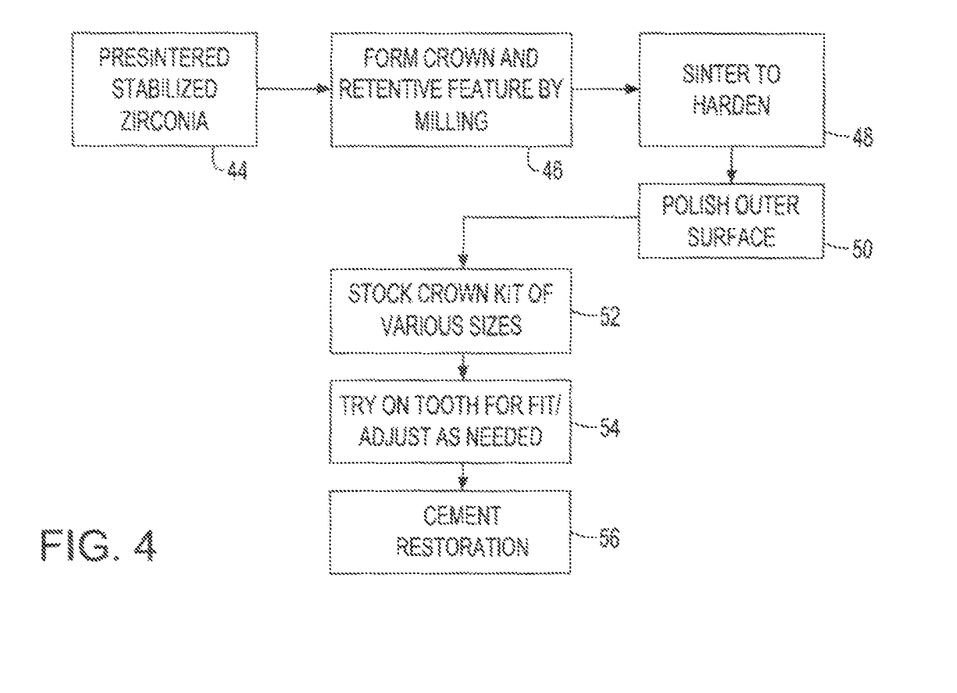
FIG. 4 is a block diagram depicting the general process for creating a zirconium crown.

It should be realized that crowns 10 or 10A of the present invention may be formed by various methods, including CAD/CAM machining, electrophoretic deposition, ceramic injection molding or slip casting. The most preferred method is by CAD/CAM machining. According to this process, as shown in FIG. 4, a presintered block of stabilized zirconia is obtained, step 44, and then precisely machined using CAD/CAM machining to form the crown and any desired retention features, step 46. The crown is then conventionally sintered to harden the stabilized zirconia, step 48. The outer surface of the crown is then polished with a polishing material such as a diamond paste to result in a pearlescent appearance, step 50.

The process continues by storing the crown in a kit of various sizes, step 52. Thereafter, the crown may be retrieved from the kit for placement on a tooth, step 54. The crown is tried on the patient's tooth for fit and adjusted as necessary. If this crown has an unsatisfactory fit, the process continues by selecting another crown. When the fit of the crown is satisfactory, the crown is cemented into place, step 56

Figure 5:
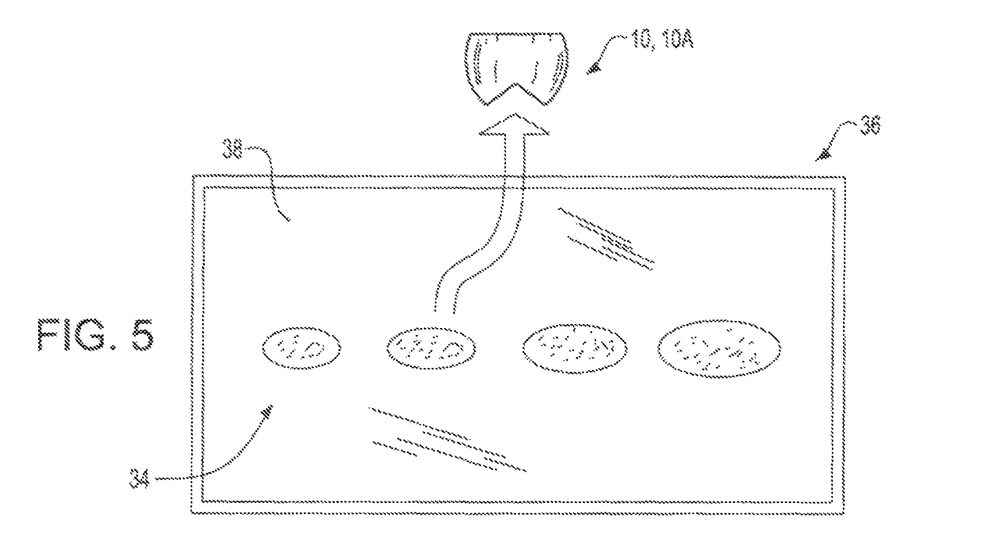
FIG. 5 is a top plan view of a kit having pedodontic crowns of various sizes which may be employed through a process selection.

Turning now to FIG. 5, there is represented a kit 36 in which a plurality of zirconia crowns 34, fabricated according to the present invention, and of various sizes are displayed on tray 38. The dental practitioner may select a particular crown 10, 10A for a particular use and insert the same over the stub 12, FIG. 1, of the natural tooth quickly and easily without taking a mold of each and every pre-existing tooth to be crowned and milling a new tooth through a CAD/CAM process, or the like. It should be realized that the system of the present invention saves time and is more economical than the prior methods found in the pedodontic and veterinarian fields.

While the present invention has particular application to pediatric and veterinary dentistry because of the lack of a suitable dental crown for these applications on the market today, the present invention nevertheless is also suitable for prefabricated crowns for adults.

The following Examples are intended to illustrate the invention of the present application but are not deemed to limit the scope of the invention in any manner.

Example I

The shape of a natural tooth was designed in CAD. From such design, a hardened zirconia block was milled to produce a crown which mimicked a natural tooth. The zirconia block consisted of pure zirconia stabilized by yttria sold under the designation "ZS-blank" by Kabo Dental Corporation, Lake Zurich, Ill. Following such production of the crown, it was pre-polished by applying a diamond impregnated silicon wheel (CERAGLAZE 1, NTI Axis Dental) to remove all surface irregularities. A final polish was achieved with a Robinson brush/wheel and a 40 millimicron diamond paste. (Frontier Dental Laboratories, El Dorado Hills, Calif.).

Example II

A crown prepared according to Example I was placed in the mouth of a child patient. A dental practitioner prepared the natural tooth using standard guidelines for primary dentition to allow the patient to receive the pre-fabricated crown of Example I. That is to say, a stub similar to stub 12 of FIG. 1 was created. The prepared zirconia crown was of the proper size having an acceptable mesiodistal width. The fit of the crown was evaluated and possible tissue impingement was determined. Extension of gingival margin was trimmed with a fine diamond wheel on slow speed with a copious water spray. The crown was filled with glass ionomer to cement the same to the natural stub of the tooth. It should be realized that self-cure composite resin cement may have also been used in this regard. The crown was then seated in the mouth completely. Practitioner then checked and adjusted occlusion. Finally, the final polish was applied to the crown using a diamond impregnated silicon wheel.

Example III

To attain a natural appearance of the crown of Examples I and II, a pre-polish was applied to all external surfaces to remove surface irregularities. A diamond impregnated silicon wheel (CERAGLAZE I, NTI Axis Dental) was employed. After such pre-polish, a final polish was accomplished by using a Robinson brush wheel with 40 ml diamond paste (Frontier Dental Laboratories of Eldorado Hills of California). The finished dental crown appeared to very closely resemble, on an aesthetic basis, the natural tooth of a human.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A method for restoration of baby teeth of a child patient through use of dental crowns, the method including the steps of:
preparing a baby tooth in a child patient for receiving a dental crown upon the baby tooth;
selecting a dental crown to be placed on the baby tooth, the dental crown selected from a kit of pre-fabricated dental crowns, the pre-fabricated dental crowns having various sizes, the dental crowns formed of a monolithic core consisting essentially of stabilized zirconia;
applying a cement between the prepared baby tooth and the dental crown of said selecting a dental crown step;
passively fitting the dental crown with the cement onto the baby tooth of said preparing a baby tooth step;
said selecting a dental crown step including the dental crowns in the kit of pre-fabricated dental crowns having an open interior chamber bounded by an inner surface;
said selecting a dental crown step including choosing a dental crown from the kit of pre-fabricated dental crowns with an open interior chamber larger than the baby tooth of said preparing a baby tooth step;
said selecting a dental crown step including the dental crowns of said kit of pre-fabricated dental crowns having at least one retention aperture formed in the inner surface;
said applying a cement step including the cement passing at least partially into the retention aperture, either during said applying a cement step or during said passively fitting step;
said selecting a dental crown step including the dental crowns in the kit of pre-fabricated dental crowns having a wall thickness of less than about half a millimeter at a margin thereof, around a circumference of an opening into the open interior of the crown;
said selecting a dental crown step including at least two related pre-fabricated dental crowns each shaped to fit over posterior baby teeth and each having a similar buccolingual dimension but having differing mesiodistal dimensions, to provide the two related crowns as a standard size crown and a narrower crown;
determining if posterior baby teeth spacing indicates use of a standard size crown or a narrower crown; and
said selecting a dental crown step including selecting a posterior crown from the at least two related pre-fabricated dental crowns having a more desirable mesiodistal dimension.

2. The method of claim 1 wherein said selecting a dental crown step includes the dental crowns in the kit of pre-fabricated dental crowns having a wall thickness of between about 0.1 mm and about 0.4 mm.

3. The method of claim 1 wherein said selecting a dental crown step includes the dental crowns in the kit of pre-fabricated dental crowns having a wall thickness of less than about 0.8 mm between the inner surface and an outer surface opposite the inner surface, and on portions of the wall spaced from the margin.

4. The method of claim 1 wherein said selecting a dental crown step includes the crowns of said kit of pre-fabricated dental crowns being free of any porcelain or plastic veneer on an exterior surface of the crowns and with a glaze directly upon the monolithic core, the glaze only partially covering the exterior surface of the monolithic core.

5. The method of claim 4 wherein the stabilized zirconia comprises zirconia and a stabilizer selected from the group consisting of magnesium oxide (MgO), calcium oxide (CaO), yttrium oxide ($Y_2O_3$), cerium oxide ($CeO_2$), aluminum oxide ($Al_2O_3$), scandium oxide ($Sc_2O_3$), ytterbium oxide ($Yb_2O_3$) and hafnium oxide ($HfO_2$).

6. The method of claim 4 wherein said stabilized zirconia comprises 85 to 99.9 weight percent zirconia and 0.1 to 15 weight percent of a stabilizer selected from the group consisting of magnesium oxide (MgO), calcium oxide (CaO), yttrium oxide ($Y_2O_3$), cerium oxide ($CeO_2$), aluminum oxide ($Al_2O_3$), scandium oxide ($Sc_2O_3$), ytterbium oxide ($Yb_2O_3$) and hafnium oxide ($HfO_2$).

7. The method of claim 1 wherein said retention aperture includes at least one groove in the inner surface.

8. A method for restoration of baby teeth of a child patient through use of dental crowns, the method including the steps of:
preparing a baby tooth in a child patient for receiving a dental crown upon the baby tooth;
selecting a dental crown to be placed on the baby tooth, the dental crown selected from a kit of pre-fabricated dental crowns, the pre-fabricated dental crowns having various sizes, the dental crowns formed of a monolithic core consisting essentially of stabilized zirconia;
applying a cement between the prepared baby tooth and the dental crown of said selecting a dental crown step;
passively fitting the dental crown with the cement onto the baby tooth of said preparing a baby tooth step;
said selecting a dental crown step including the dental crowns in the kit of pre-fabricated dental crowns having an open interior chamber bounded by an inner surface;
said selecting a dental crown step including choosing a dental crown from the kit of pre-fabricated dental crowns with an open interior chamber larger than the baby tooth of said preparing a baby tooth step;
said selecting a dental crown step including the dental crowns of said kit of pre-fabricated dental crowns having at least one retention aperture formed in the inner surface;
said applying a cement step including the cement passing at least partially into the retention aperture, either during said applying a cement step or during said passively fitting step;
said selecting a dental crown step including at least two related pre-fabricated dental crowns each shaped to fit over posterior baby teeth and each having a similar buccolingual dimension but having differing mesiodistal dimensions, to provide the two related crowns as a standard size crown and a narrower crown;
determining if posterior baby teeth spacing indicates use of a standard size crown or a narrower crown; and
said selecting a dental crown step including selecting a posterior crown from the at least two related pre-fabricated dental crowns having a more desirable mesiodistal dimension.

9. The method of claim 8 wherein said selecting a dental crown step includes the dental crowns in the kit of pre-fabricated dental crowns having a wall thickness of less than about 0.8 mm between the inner surface and an outer surface opposite the inner surface, and on portions of the wall spaced from the margin.

10. The method of claim 8 wherein said selecting a dental crown step includes the crowns of said kit of pre-fabricated dental crowns being free of any porcelain or plastic veneer on an exterior surface of the crowns and with a glaze directly upon the monolithic core, the glaze only partially covering the exterior surface of the monolithic core.

11. The method of claim 10 wherein said stabilized zirconia comprises zirconia and a stabilizer selected from the group consisting of magnesium oxide (MgO), calcium oxide (CaO), yttrium oxide ($Y_2O_3$), cerium oxide ($CeO_2$), aluminum oxide ($Al_2O_3$), scandium oxide ($Sc_2O_3$), ytterbium oxide ($Yb_2O_3$) and hafnium oxide ($HfO_2$).

12. The method of claim 10 wherein the stabilized zirconia comprises 85 to 99.9 weight percent zirconia and 0.1 to 15 weight percent of a stabilizer selected from the group consisting of magnesium oxide (MgO), calcium oxide (CaO), yttrium oxide ($Y_2O_3$), cerium oxide ($CeO_2$), aluminum oxide ($Al_2O_3$), scandium oxide ($Sc_2O_3$), ytterbium oxide ($Yb_2O_3$) and hafnium oxide ($HfO_2$).

13. A method for restoration of baby teeth of a child patient through use of dental crowns, the method including the steps of:
preparing a baby tooth in a child patient for receiving a dental crown upon the baby tooth;
selecting a dental crown to be placed on the baby tooth, the dental crown selected from a kit of pre-fabricated dental crowns, the pre-fabricated dental crowns having various sizes, the dental crowns formed of a monolithic core consisting essentially of stabilized zirconia;
applying a cement between the prepared baby tooth and the dental crown of said selecting a dental crown step;
passively fitting the dental crown with the cement onto the baby tooth of said preparing a baby tooth step;
said selecting a dental crown step including the dental crowns in the kit of pre-fabricated dental crowns having an open interior chamber bounded by an inner surface;
said selecting a dental crown step including choosing a dental crown from the kit of pre-fabricated dental crowns with an open interior chamber larger than the baby tooth of said preparing a baby tooth step;
said selecting a dental crown step including the dental crowns of said kit of pre-fabricated dental crowns having at least one retention aperture formed in the inner surface;
said applying a cement step including the cement passing at least partially into the retention aperture, either during said applying a cement step or during said passively fitting step; and
said selecting a dental crown step including the dental crowns in the kit of pre-fabricated dental crowns having a wall thickness of less than about half a millimeter at a margin thereof around a circumference of an opening into the open interior of the crown.

14. The method of claim 13 wherein said selecting a dental crown step includes the dental crowns in the kit of pre-fabricated dental crowns having a wall thickness of between about 0.1 mm and about 0.4 mm.

15. The method of claim 13 wherein said selecting a dental crown step includes the dental crowns in the kit of pre-fabricated dental crowns having a wall thickness of less than about 0.8 mm between the inner surface and an outer surface opposite the inner surface, on portions of the wall spaced from the margin.

16. The method of claim 13 wherein said selecting a dental crown step includes the crowns of said kit of pre-fabricated dental crowns being free of any porcelain or plastic veneer on an exterior surface of the crowns and with a glaze directly upon the monolithic core, the glaze only partially covering the exterior surface of the monolithic core.

17. The method of claim 16 wherein the stabilized zirconia comprises zirconia and a stabilizer selected from the group consisting of magnesium oxide (MgO), calcium oxide (CaO), yttrium oxide ($Y_2O_3$), cerium oxide ($CeO_2$), aluminum oxide ($Al_2O_3$), scandium oxide ($Sc_2O_3$), ytterbium oxide ($Yb_2O_3$) and hafnium oxide ($HfO_2$).

18. The method of claim 16 wherein the exterior surface of the core comprises a front exterior surface and a rear exterior surface and wherein the dental crown is for an anterior tooth and the glaze covers only the front exterior surface of the core.

19. The method of claim 16 wherein the exterior surface of the core comprises a front exterior surface and a rear exterior surface and wherein the dental crown is for a posterior tooth and the glaze covers only a portion of the front exterior surface of the core and only a portion of the rear exterior surface of the core.

20. The method of claim 16 wherein the core has a biting surface and the biting surface is devoid of the glaze.

* * * * *